United States Patent [19]

Keith et al.

[11] 4,350,707

[45] Sep. 21, 1982

[54] INACTIVATION OF LIPID CONTAINING VIRUSES WITH BUTYLATED HYDROXYTOLUENE

[75] Inventors: Alec D. Keith, Boalsburg; Wallace Snipes, Pine Grove Mills, both of Pa.

[73] Assignee: Research Corporation, New York, N.Y.

[21] Appl. No.: 655,413

[22] Filed: Feb. 5, 1976

[51] Int. Cl.³ .............................................. A61K 31/05
[52] U.S. Cl. ..................................... 424/346; 424/89; 424/93
[58] Field of Search ................. 260/624 R; 424/89,93, 424/346

[56] References Cited

U.S. PATENT DOCUMENTS 2,081,284  5/1937  Stockelbach ..................... 260/624 R

FOREIGN PATENT DOCUMENTS 1302984  7/1962  France .
47274  4/1966  German Democratic Rep. .

OTHER PUBLICATIONS

Snipes, Science, vol. 188, Apr. 4, 1975; pp. 64–66.
Cupp, Antimicrobial Agents & Chemotherapy, vol. 8; No. 6, Dec. 1975, pp. 698–705.
Emanuel, Chem. Abs., vol. 52, 1958, p. 20643c.
Kajimoto, Chem. Abs., vol. 61, 1964, pp. 13797c–13797j.
Sands, Chem. Abs., vol. 61, 1964, p. 989j.
Dolyagin, Chem. Abs., vol. 74, 1971, No. 20492t.
De Navarre, The Chem. & Mfg. of Cosmetics, D. Van Nostrand Co., N.Y., 2nd Ed., vol. I, 1962, pp. 300, 305–313.

Primary Examiner—Anna P. Fagelson
Attorney, Agent, or Firm—Finnegan, Henderson, Farabow, Garrett & Dunner

[57] ABSTRACT

Inactivation of, and treatment of diseases caused by, lipid containing viruses, particularly herpes simplex virus, with butylated hydroxytoluene.

10 Claims, 1 Drawing Figure

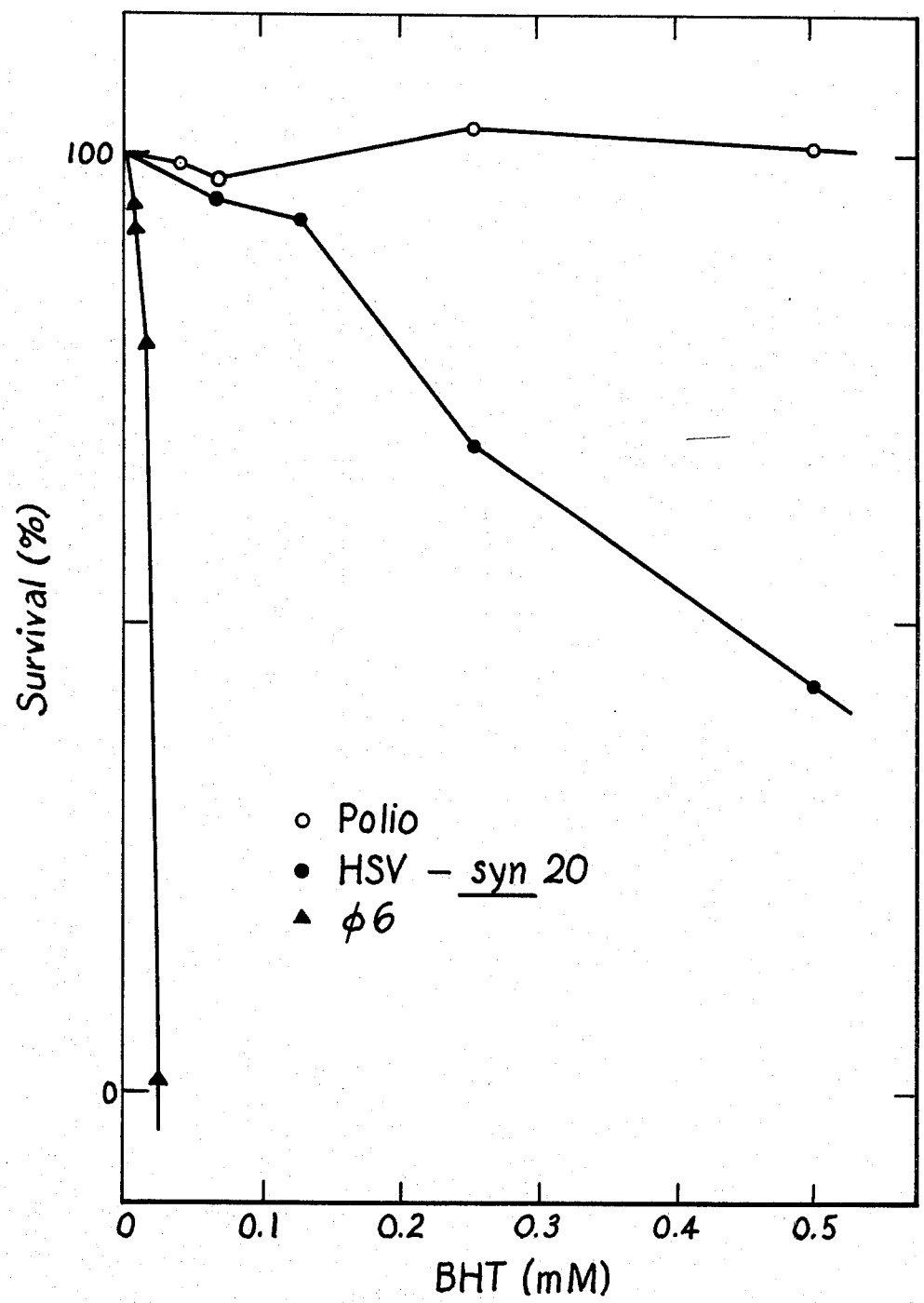

INACTIVATION OF LIPID CONTAINING VIRUSES WITH BUTYLATED HYDROXYTOLUENE

The invention described herein was made in the course of work under a grant or award from the Department of Health, Education and Welfare.

FIELD OF INVENTION

This invention relates to new and useful improvements in the inactivation of lipid-containing viruses and more particularly seeks to provide an effective treatment of diseases caused by said viruses with butylated hydroxytoluene, hereinafter called BHT, having the well-known molecular structure:

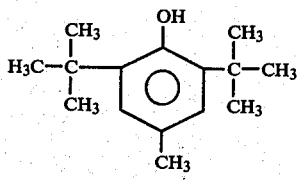

PRIOR ART—VIRUSES

In the late thirties and early forties, the medical community achieved a large measure of control over bacterial infections of animals with the discovery that sulfonamide and penicillin compounds of minor toxicity to a host would effectively inactivate or prevent the growth of many species of bacteria. Since that time, many other antibiotics have been found to control a wide spectrum of bacteria.

The smaller and more elusive viruses have proven more resistant to control by medical scientists. As a result, most viral-mediated diseases still remain without satisfactory medical treatments. Pathogenic viruses can be classified into two general types with respect to the viral structure, those that contain lipids and those that do not. Some well known lipid-containing pathogenic viruses are the pox viruses, the various herpes viruses, influenza viruses, C-type tumor viruses, and Newcastle's Disease virus. Many other pathogenic viruses do not contain lipids, e.g., polio and certain common colds.

Most agents currently in use or under investigation as chemical therapeutic agents against viruses operate on nucleic acid polymers. This type of treatment is medically disturbing due to the similarity of human nucleic acid polymers and those of infecting viruses. Genetic lesions may lead to resistant viral mutants and/or modified cellular DNA, either or both of which may have drastic long-term effects.

PRIOR ART—BHT

BHT is one of several antioxidants that are commonly added to foods to maintain freshness and prevent spoilage by oxidation processes. It is frequently added to dried cereals, cooking oils, canned goods, and various animal foods. It is on the Food and Drug Administration's GRAS (generally recognized as safe) list. In fact, the average daily intake of BHT in the United Stated has been estimated at 2 mg per person and it is accumulated in the body fat because it is not readily excreted.

Literature references report that BHT in large doses causes bile duct proliferation in mice, is toxic to developing insect larvae, and reduces the growth rate of cultured mammalian cells. Some individuals show chemical intolerance to BHT. On the other hand, data show that BHT reduces chemical carcinogenesis, protects against damage due to choline deficiency, protects against poisoning by carbon tetrachloride, and, under certain conditions, retards aging in mice. It is also applied topically in cosmetic preparations.

It has been reported, based on a small sample, that United States residents, because of the previously mentioned consumption and excretion factors, have $1.30 \pm 0.82$ parts per million of BHT in body fat tissue. What effect this may have on viruses hosted by humans is not known. Higher levels, and in non-fat tissue, could be achieved by ingestion orally or systemically of larger amounts of BHT than normally consumed as food additives.

The effectiveness of BHT as an antioxidant for certain foods is probably due in good part to its high solubility in fats and its extremely low solubility in water. This places the BHT molecule in regions where its antioxidant activity is most effective in preventing rancidity. These same hydrophobic characteristics, when considered for living systems, suggest that BHT may have strong interactions with the hydrocarbon zones of membrane structures, and perturbing effects of BHT on membrane associated function, have, in fact, been observed by Metcalfe, 23 J. Pharm. Pharmac. 817 (1971) and Eletr et al., 339 Biochim. Biophys. Acta. 190 (1974). The interaction of BHT with membranes and the results of this interaction are very likely distinct from and independent of its antioxidizing action.

SUMMARY OF THE INVENTION

We have unexpectedly found that BHT is surprisingly effective in the inactivation of lipid-containing viruses. BHT has been shown effective against such lipid-containing viruses as herpes simplex, $\phi 6$ and PM2 but ineffective against such non-lipid viruses as polio and $\phi 23$-1-a. We have further found that BHT is effective in reducing the duration of or controlling the start of herpes simplex skin lesions on humans and eye infections in rabbits.

BRIEF DESCRIPTION OF THE DRAWING

The FIGURE is a graph demonstrating results achieved with the present invention.

DETAIL OF PREFERRED EMBODIMENT

In vitro studies have been made with herpes simplex virus type 1, strain KOS (hereinafter HSV); a syncytial-formal mutant derived from the KOS strain, designated HSV-syn 20; polio virus, type 2, attenuated, P712 ch2ab; PM2 (a bacteriophage) isolated by Espejo et al., 34 Virology 738 (1968); $\phi 6$ (bacterial virus) isolated by Vidaver et al., 11 J. Virol. 799 (1973); and $\phi 23$-1-a isolated by Vidaver. Both $\phi 6$ and $\phi 23$-1-a infect the plant pathogen Pseudomonas phaseolicola strain HB10Y.

Virus stocks were diluted to approximately (2 to 4)$\times 10^7$ plaque-forming units per milliliter in appropriate buffered solutions. A 0.1-ml portion of BHT in different molar solutions in 95% ethanol was mixed with 5 ml of buffer, and then added to a 5-ml sample of the virus. After 30 minutes, the samples were diluted and assayed for plaque-forming units on appropriate host cells. The results are observed in the figure of the drawing which is a logarithmic graph where % survival is plotted against BHT concentration in milli-molar that was present during the 30 minute exposure.

Under the testing conditions, this clearly demonstrates BHT effectiveness against the two lipid-containing viruses, $\phi 6$ and HSV-syn 20 and ineffectiveness against the non-lipid containing polio virus.

Further testing with similar solutions was then conducted to show the BHT concentration required to inactivate 50% of a given virus, the results of which are shown in the following table:

| Virus | Lipid % | BHT conc. (M) |
|---|---|---|
| $\phi 6$ | 25 | $10^{-5}$ |
| HSV | 22 | $0.7 \times 10^{-4}$ |
| HSV-syn 20 | 22 | $1.6 \times 10^{-4}$ |
| PM2 | 13 | $10^{-4}$ |
| $\phi 23$-1-a | none | $>5 \times 10^{-4}$ |
| Polio | none | $>5 \times 10^{-4}$ |

Here again the effectiveness is demonstrated only against the lipid-containing viruses, no tests having been run above $5 \times 10^{-4}$ (M) BHT concentration. It is interesting to note the difference between $\phi 6$ and $\phi 23$-1-a which normally infect the same host.

Laboratory experiments carried out on human or bacterial cells are all carried out in aqueous media. While the metabolic functions of cells are also carried out in an aqueous medium there remain some important considerations in getting BHT to the site of viral infection. In the test tube case, with isolated virus, the BHT must diffuse through water until it comes in contact with a surface or zone which has more suitable solubility properties such as a viral or cell membrane. Therefore, the delivery of BHT molecules to these sites is a requirement in order for BHT to be effective as an antiviral agent. Application of BHT to an infected tissue surface also has the problem of delivery of adequate BHT to inactivate the viral agents. Due to the low solubility of BHT in water a more suitable solvent must be used. Ideally the carrier solvent would be saturated with BHT and upon application to an infected area the BHT would exchange to the viral and cell membrane. Due to these considerations we have adopted various solvent mixtures including those shown below for application to skin and mucous membrane areas (% by weight).

| | % | % | Range % |
|---|---|---|---|
| BHT | 5 | 10 | 1-saturation (about 10%) |
| Ethanol | 50 | 47 | 40–60 |
| Propylene glycol | 37 | 35 | 30–45 |
| Water | 3 | 3 | 0–5 |
| Tween 20* | 5 | 5 | 0–8 |

*Atlas Chemical Industries trademark for monolaurate ethoxylated ester of sorbitan (20 units oxyethylene/ester mole), a mild non-irritating detergent.

Care must be taken to keep the container closed as evaporation may cause the BHT to precipitate. Other solvent carriers are 1% to saturation (about 20%) of BHT in mineral oil or petrolatum.

Twenty patients suffering with chronic recurring herpes on varying body sites, including lips, hands and genitalia were treated with the above ethanol solutions of BHT. The average previous episode in these patients lasted seven days from first eruptions of a vesicle until complete clearing. Starting with appearance of the vesicles, the patients applied small amounts of the above formulations directly to the infected area four times daily. In eighteen patients, the duration was diminished to an average of three days. There was no appreciable difference in the other two patients.

Thirty rabbits were divided into three groups and the eyes of all treated with cultured herpes simplex virus. A control group was not further treated, a second group was treated with iododeoxyuridine (IDU), which is accepted as an effective form of therapy for herpes infection of the eyes, and the third group was treated with a 5% solution of BHT in mineral oil. After 4 days, the eyes of the BHT and IDU groups were controlled and comparable, whereas the infection was progressive in the non-treated group.

For topical application of the non-toxic BHT, concentration in the carrier is not as important as total amount applied. Saturated solutions, however, decrease dilution of the BHT and increase transfer to the virus cells. Other appropriate pharmaceutical carriers may be used, bearing in mind the hydrophobic nature of BHT and sensitivity of tissue to be treated. Generally long polymers with hdyrocarbon side groups dissolve BHT but do not irritate tissues. A 1% solution is generally a minimum but 5–20% or up to saturation of a particular carrier is preferred.

Herpes simplex infections occur and recur at many areas and organs of the body, but particularly the skin and mucocutaneous areas. The most common sites are face (particularly around the lips) and neck, followed by anogenital area and then the sacrum and buttocks. It is seen anywhere on the skin including ears, nose, chest, abdomen, arms, palms, dorsa of the hands, fingers, thighs and legs. Other common sites are the eyes and cervix. Less often involved but observed are the mouth, respiratory tract and central nervous system. The BHT compositions herein are designed for topical application to all skin areas, eyes and mucocutaneous area such as lips, nares, prepuce, glans penis, cervix and vaginal tract. Mineral oil and petrolatum carriers are generally used with the more sensitive treatment areas.

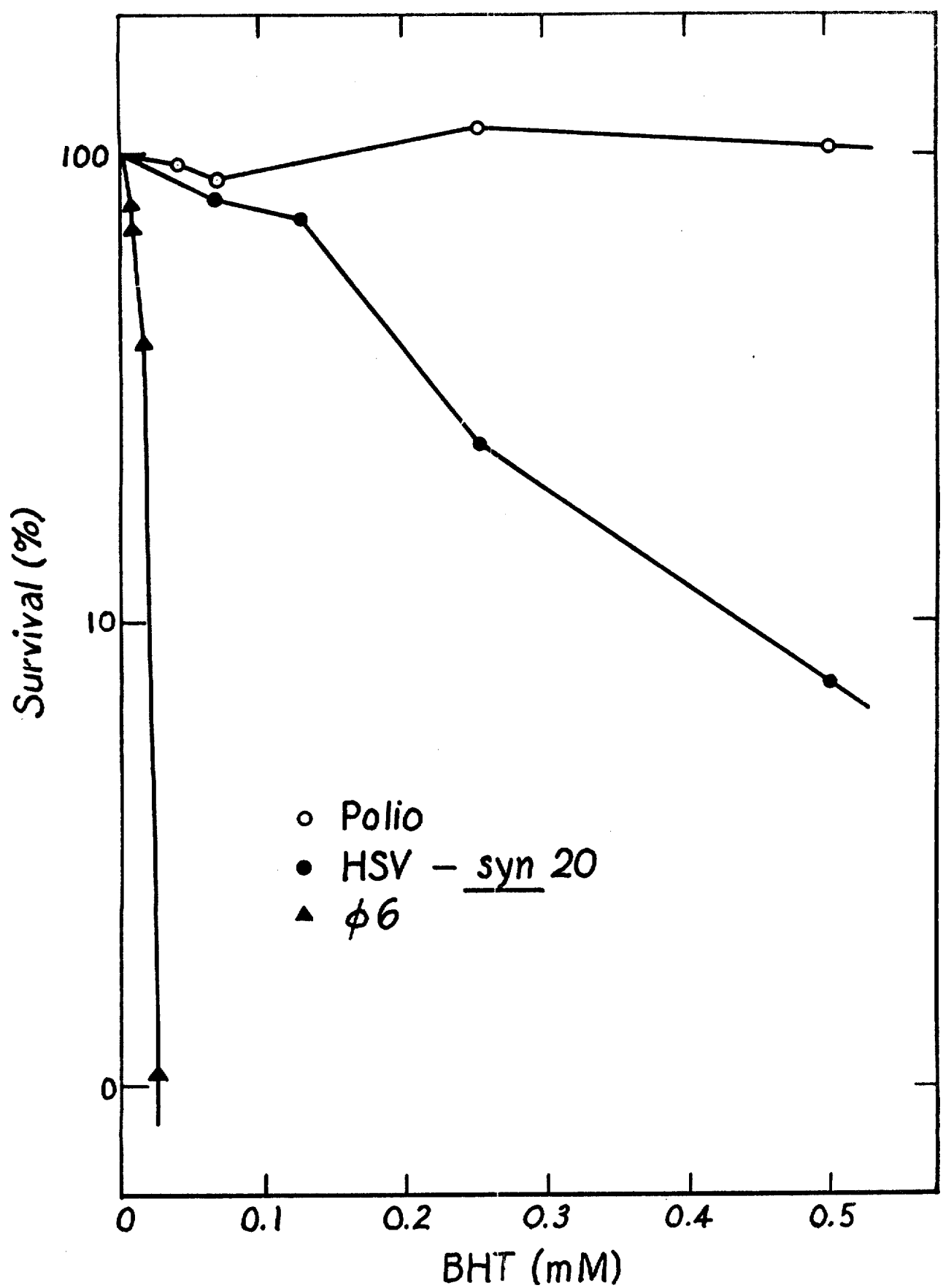

We claim:

1. A method for treating a subject having a disease caused by lipid-containing viruses comprising administering to said subject an effective inactivating amount therefor of butylated hydroxytoluene in a non-toxic, pharmaceutically acceptable barrier.

2. A method according to claim 1, wherein the concentration of said butylated hydroxytoluene in said carrier is 1% to saturation.

3. A method according to claim 2, wherein said pharmaceutically acceptable carrier is mineral oil.

4. A method according to claim 2, wherein said pharmaceutically acceptable carrier is 40 to 60% ethanol, 30 to 45% propylene glycol, 0 to 5% water, and 0 to 8% monolaurate ethoxylated (20 units/mole) ester of sorbitan.

5. A method according to claim 2, wherein the affected area is skin, eyes and mucocutaneous areas including lips, nares, prepuce, glans penis and cervix.

6. A method according to claim 5, wherein the affected skin area is the hands, face, neck or external genitalia.

7. A method according to claim 2, wherein said virus is a herpes simplex virus.

8. A method according to claim 7, wherein said disease is an eye disease caused by herpes simplex and the butylated hydroxytoluene is applied topically thereto.

9. The method according to claim 7, wherein said disease is a topical infection caused by herpes simplex in man and the butylated hydroxytoluene is applied topically to the infected areas.

10. A method for inactivating lipid-containing viruses comprising exposing said viruses to an effective inactivating amount of butylated hydroxytoluene in a non-toxic pharmaceutically acceptable carrier.

* * * * *

UNITED STATES PATENT AND TRADEMARK OFFICE
CERTIFICATE OF CORRECTION

PATENT NO. : 4,350,707            Page 1 of 2
DATED : September 21, 1982
INVENTOR(S) : ALEC D. KEITH ET AL It is certified that error appears in the above-identified patent and that said Letters Patent are hereby corrected as shown below:

The sheet of drawing has been corrected to read as per attached sheet.

Signed and Sealed this

Eighth Day of March 1983

[SEAL]

Attest:

Attesting Officer

GERALD J. MOSSINGHOFF
Commissioner of Patents and Trademarks